United States Patent

Dale

(10) Patent No.: US 9,157,975 B2
(45) Date of Patent: Oct. 13, 2015

(54) CONCURRENT FAT AND IRON ESTIMATION IN MAGNETIC RESONANCE SIGNAL DATA

(71) Applicant: Brian Dale, Morrisville, NC (US)

(72) Inventor: Brian Dale, Morrisville, NC (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 196 days.

(21) Appl. No.: 14/061,798

(22) Filed: Oct. 24, 2013

(65) Prior Publication Data

US 2014/0114178 A1 Apr. 24, 2014

Related U.S. Application Data

(60) Provisional application No. 61/717,662, filed on Oct. 24, 2012.

(51) Int. Cl.
| | |
|---|---|
| *A61B 5/055* | (2006.01) |
| *G01R 33/48* | (2006.01) |
| *G01R 33/56* | (2006.01) |
| *G01R 33/50* | (2006.01) |
| G01R 33/485 | (2006.01) |

(52) U.S. Cl.
CPC ............ *G01R 33/4828* (2013.01); *A61B 5/055* (2013.01); *G01R 33/50* (2013.01); *G01R 33/5608* (2013.01); *G01R 33/485* (2013.01)

(58) Field of Classification Search
CPC ........ A61B 5/05; A61B 5/055; A61B 5/4244; A61B 5/4869; A61B 5/4872; G01R 33/50; G01R 33/4828

USPC .................................................. 600/407, 410
See application file for complete search history.

(56) References Cited

U.S. PATENT DOCUMENTS

| | | | | |
|---|---|---|---|---|
| 4,889,125 | A * | 12/1989 | Doddrell et al. | 600/410 |
| 5,322,682 | A * | 6/1994 | Bartzokis et al. | 600/410 |
| 8,824,766 | B2 * | 9/2014 | Bashir et al. | 382/131 |
| 2001/0029329 | A1* | 10/2001 | Avrin et al. | 600/407 |
| 2005/0020904 | A1* | 1/2005 | Cline et al. | 600/410 |
| 2005/0215882 | A1* | 9/2005 | Chenevert et al. | 600/410 |
| 2007/0161887 | A1* | 7/2007 | Marinelli | 600/409 |
| 2008/0039708 | A1* | 2/2008 | Taicher et al. | 600/410 |
| 2009/0093704 | A1* | 4/2009 | Ma | 600/410 |

* cited by examiner

*Primary Examiner* — Peter Luong
(74) *Attorney, Agent, or Firm* — Peter R. Withstandley (57) ABSTRACT

A computer-implemented method for concurrently estimating the amount of fat and iron in anatomical tissue from magnetic resonance (MR) signal data includes receiving a test signal representative of the anatomical tissue acquired using a MR pulse sequence type. A repository of reference signal data is generated. The repository comprises a plurality of reference signals derived by an MR signal simulation for a plurality of different transverse relaxation rates, a plurality of different fat fractions, and the MR pulse sequence type. A first reference signal is identified in the plurality of reference signals. The first reference signal provides a best match to the test signal based on one or more matching criteria. The repository is searched to determine a first transverse relaxation rate and a first fat fraction associated with the first reference signal. Then, the amount of fat and iron in the anatomical tissue is estimated based on the first transverse relaxation rate and the first fat fraction.

20 Claims, 4 Drawing Sheets

CONCURRENT FAT AND IRON ESTIMATION IN MAGNETIC RESONANCE SIGNAL DATA

CROSS-REFERENCE TO RELATED APPLICATIONS

This application claims priority to U.S. provisional application Ser. No. 61/717,662 filed Oct. 24, 2012 which is incorporated herein by reference in its entirety.

TECHNICAL FIELD

The present invention relates generally to methods, systems, and apparatuses for concurrently estimating fat and iron by generating a library of reference signals corresponding to different amounts of fat and iron and using matching criteria to concurrently estimate both the fat and iron in a magnetic resonance signal. The disclosed methods, systems, and apparatuses may be applied to, for example, provide concurrent fat and iron measurements for use in the treatment of hepatic diseases.

BACKGROUND

Certain clinical conditions can result in an accumulation of fat in the liver. The amount of fat in the liver can be quantified using various magnetic resonance (MR) chemical-shift imaging methods, such as Dixon or spectroscopy. Other clinical conditions can result in an accumulation of various metal species, such as iron or copper, in the liver. The amount of iron in the liver can be correlated using various MR relaxation methods including, for example, multi-echo gradient echo (GRE) methods. In patients where both types of clinical conditions are present, the iron can interfere with quantification of the fat and the fat can interfere with estimation of the iron. Consequently, the concurrent estimation of fat and iron is a challenging task.

Conventional systems use an estimated fat value to perform fat-corrected iron estimation. Then, the iron estimation is used to perform an iron-corrected fat estimation in an iterative manner until a criterion is reached. While this process addresses some of the difficulties involved in fat and iron estimation, the use of iteration is burdensome and error prone. Thus, it is desirable estimate fat and iron concurrently without requiring any iteration between fat and iron estimation methods.

SUMMARY

Embodiments of the present invention address and overcome one or more of the above shortcomings and drawbacks, by providing methods, systems, and apparatuses for generating a library of reference signals corresponding to different amounts of fat and iron and using matching criteria to concurrently estimate both the fat and iron in an MR test signal. This technology is particularly well-suited for, but by no means limited to, quantifying fat and iron deposition for the treatment of hepatic diseases.

According to some embodiments of the present invention, a computer-implemented method for concurrently estimating an amount of fat and iron in anatomical tissue from magnetic resonance (MR) signal data includes receiving a test signal representative of the anatomical tissue acquired using a MR pulse sequence type. Next, a repository of reference signal data is generated. This repository comprises a plurality of reference signals derived by an MR signal simulation for a plurality of different transverse relaxation rates, a plurality of different fat fractions, and the MR pulse sequence type. The MR signal simulation may include, for example, application of a Bloch function for magnetic resonance. A first reference signal is identified in the plurality of reference signals, the first reference signal providing a best match to the test signal based on one or more matching criteria. For example, in one embodiment, the one or more matching criteria comprise a measure of signal similarity determined by a mathematical product calculation. Next, the repository is searched to determine a first transverse relaxation rate and a first fat fraction associated with the first reference signal. The amount of fat and iron in the anatomical tissue may then be estimated based on the first transverse relaxation rate and the first fat fraction.

Embodiments of the present invention provide additional features which further supplement, enhance, and/or refine the aforementioned method. For example, in one embodiment, identifying the first reference signal in the plurality of reference signals in the aforementioned method is performed by calculating a mathematical product value of the test signal with the respective reference signal for each of the plurality of reference signals. Then, the first reference signal is identified by determining that it has a maximum mathematical product value among the plurality of reference signals. In another embodiment, the method further includes generating a plurality of magnetic field offset values corresponding to the different transverse relaxation rates and storing the plurality of magnetic field offset values in the repository of reference signal data. In some embodiments, the method further includes generating an incoherent set of echo times for use in acquiring the reference signals and deriving the reference signals by the MR signal simulation at the incoherent set of echo times. These echo times may be used, for example, when acquiring the test signal.

According to other embodiments of the present invention, a system for concurrently estimating an amount of fat and iron in anatomical tissue from MR signal data comprises an input processor, a repository of reference signal data, and an image data processor. The input processor is configured to receive a test signal representative of the anatomical tissue acquired using a MR pulse sequence type. The repository of reference signal data comprises a plurality of reference signals derived by MR signal simulation for a plurality of different transverse relaxation rates, a plurality of different fat fractions, and the MR pulse sequence type. The image data processor is configured to: identify a first reference signal in the plurality of reference signals providing a best match to the test signal based on one or more matching criteria; search the repository to determine a first transverse relaxation rate and a first fat fraction associated with the first reference signal; and estimate the amount of fat and iron in the anatomical tissue based on the first transverse relaxation rate and the first fat fraction.

Embodiments of the present invention provide additional features which further supplement, enhance, and/or refine the aforementioned system. For example, in one embodiment, the image data processor identifies the first reference signal in the plurality of reference signals by a matching process which includes calculating, for each of the plurality of reference signals, a mathematical product value of the test signal with the respective reference signal. The first reference signal is identified by determining that it has a maximum mathematical product value among the plurality of reference signals.

In some embodiments, the system further comprises a simulation processor configured to generate the plurality of reference signals, for example, using a Bloch function. In one embodiment, the simulation processor is further configured to generate a range of fat fraction values for corresponding transverse relaxation rate values. The simulation processor may be further configured to generate a plurality of magnetic field offset values for corresponding transverse relaxation rate values in some embodiments. In some embodiments, the simulation processor is further configured to generate an incoherent set of echo times for use in acquiring the reference signals generate the repository of reference signal data at the incoherent set of echo times using a signal model.

According to other embodiments of the present invention, a computer-implemented method for concurrently estimating fat and iron in anatomical tissue using MR signal data includes receiving, by an image processing computer, MR signal data representative of a portion of patient anatomy. The image processing computer generates a library of reference signal entries, with each reference signal entry comprising a reference signal, an associated transverse relaxation value, and an associated fat fraction value. With a received test signal, an inner product value of the test signal with each reference signal entry in the library of reference signal entries is calculated. Next, the image processing computer identifies a first reference signal entry associated with a maximum inner product value. Then, the image processing computer estimates a test transverse relaxation rate value and a test fat fraction value based on a first associated transverse relaxation value and a first associated fat fraction value corresponding to the first reference signal entry.

In some embodiments of the aforementioned method, generating the library of reference signals includes the image processing computer receiving an MR pulse sequence. The image processing computer selects a range of transverse relaxation rate values. For example, in one embodiment, the range of transverse relaxation rate values comprises a plurality of transverse relaxation rate values ranging from 0 Hz to 600 Hz in increments of 5 Hz. Then, for each transverse relaxation value in the range of transverse relaxation rate values, an iterative process is performed. In one embodiment, this process comprises selecting, by the image processing computer, a plurality of fat fraction values; performing a MR simulation to generate a reference signal for the respective transverse relaxation value and each fat fraction value; and creating a plurality of entries in the library of reference signals, each entry comprising the generated reference signal, the respective transverse relaxation value, and one of the plurality of fat fraction values. In one embodiment, each reference signal entry in the library of reference signal entries further comprises one or more magnetic field offset values.

In other embodiments of the aforementioned method, generating the library of reference signals includes the image processing computer receiving an MR pulse sequence and selecting a range of fat fraction values. For example, range of fat fraction values may comprise a plurality of fat fraction values ranging from 0% to 90% in increments of 1%. Then, for each fat fraction value in the range of fat fraction values, an iterative process is performed. This process may include, for example, selecting, by the image processing computer, a plurality of transverse relaxation values; performing a MR simulation to generate a reference signal for each transverse relaxation value and the respective fat fraction value; and creating plurality of entries in the library of reference signals, each entry comprising the generated reference signal, one of the transverse relaxation values, and the respective fat fraction value.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses for concurrently estimating fat and iron in magnetic resonance (MR) signal data. Briefly, in various embodiments, a library of reference signals is generated, with each reference signal corresponding to a different amount of fat and iron. Then, a test signal (e.g., acquired from a patient) is matched to the reference signals in the library to identify which reference signal best matches the test signal. By identifying the corresponding fat and iron values associated with the identified reference signal, the fat and iron values corresponding to the test signal may be estimated.

Figure 1:
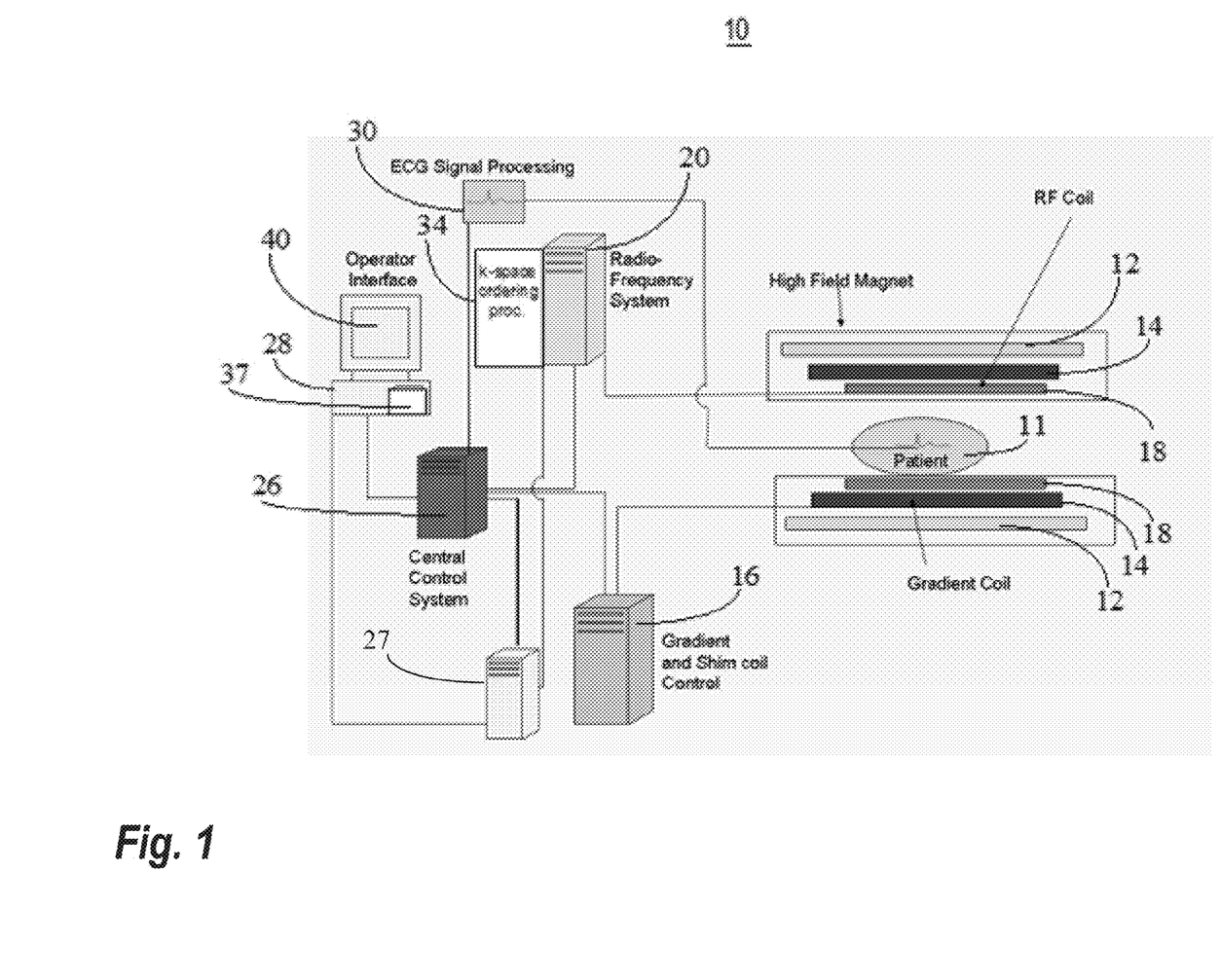
FIG. 1 shows a system for ordering acquisition of frequency domain components representing MR image data for storage in a k-space storage array, according to some embodiments of the present invention.

FIG. 1 shows a system 10 for ordering acquisition of frequency domain components representing MR image data for storage in a k-space storage array, according to some embodiments of the present invention. This system 10 may be used, for example, to acquire the test signal described in various embodiments herein. In system 10, magnet 12 creates a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shimming/pulse sequence control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further, RF (radio frequency) system 20 provides RF pulse signals to RF coil 18, which in response produces magnetic field pulses which rotate the spins of the protons in the imaged body 11 by ninety degrees or by one hundred and eighty degrees for so-called "spin echo" imaging, or by angles less than or equal to 90 degrees for so-called "gradient echo" imaging. Pulse sequence control module 16 in conjunction with RF system 20 as directed by central control system 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF system 20 and k-space component processor unit 34 to provide image representative data to an image processing computer 27 operable coupled to central control unit 26. In some embodiments, an image data processor internal to the central control unit 26 provides the functionality of the image processing computer 27, rather than having that functionality in an external unit as in FIG. 1. ECG synchronization signal generator 30 provides ECG signals used for pulse sequence and imaging synchronization. A two or three dimensional k-space storage array of individual data elements in unit 34 stores corresponding individual frequency components comprising an MR dataset. The k-space array of individual data elements has a designated center and individual data elements individually have a radius to the designated center.

A magnetic field generator (comprising magnetic coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of an MR dataset representing an MR image. A storage processor in unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control system 26 uses information stored in an internal database to process the detected MR signals in a coordinated manner to generate high quality images of a selected slice (or slices) of the body and adjusts other parameters of system 10. The stored information comprises, for example, predetermined pulse sequence and magnetic field gradient and strength data as well as data indicating timing, orientation and spatial volume of gradient magnetic fields to be applied in imaging. Generated images are presented on display 40. Computer 28 includes a graphical user interface (GUI) enabling user interaction with central controller 26 and enables user modification of magnetic resonance imaging signals in substantially real time. Display processor 37 processes the magnetic resonance signals to provide image representative data for display on display 40, for example.

Figure 2:
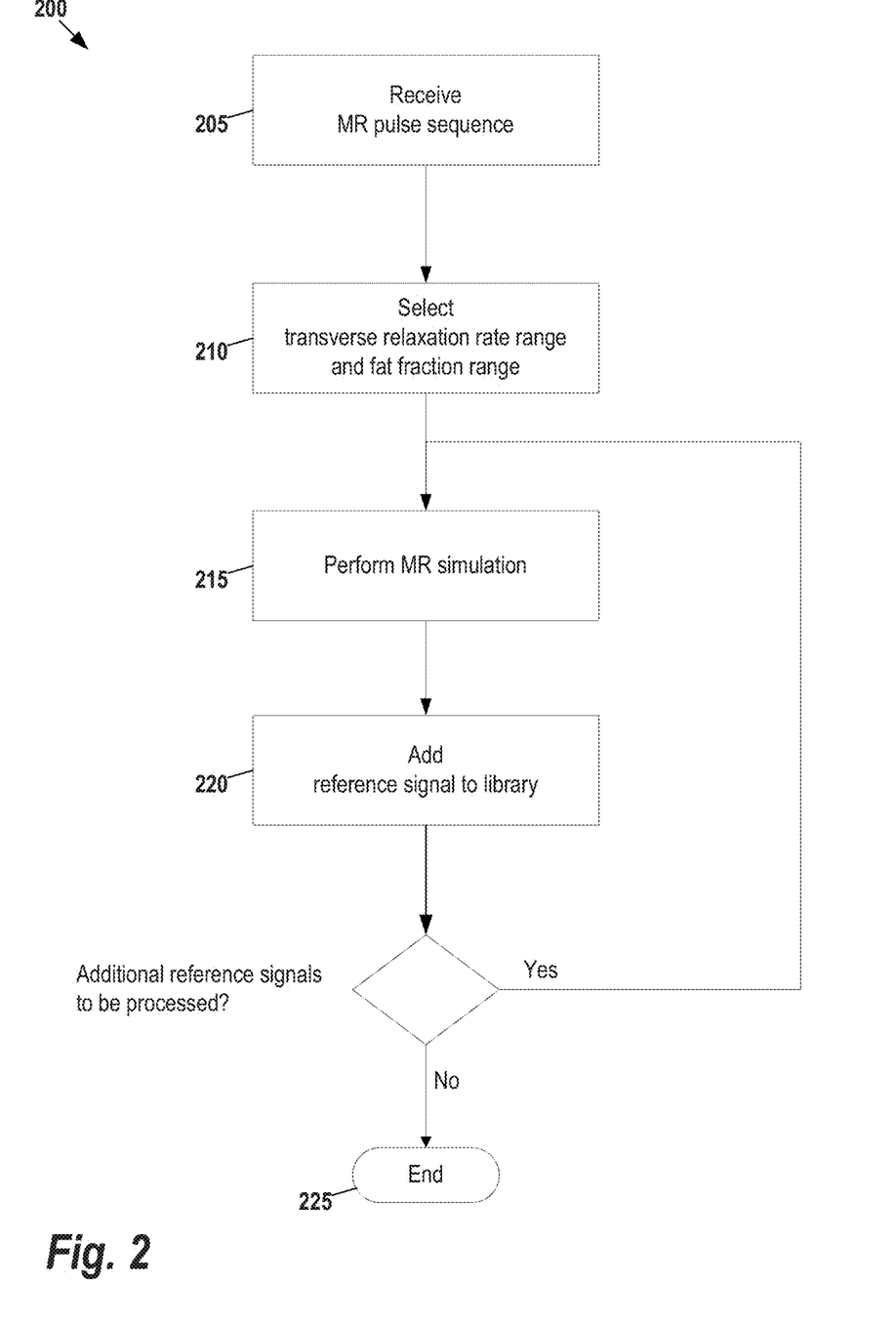
FIG. 2 provides an illustration of a process for generating a reference signal repository, according to some embodiments of the present invention.

FIG. 2 provides an illustration of a process 200 for generating a reference signal repository, according to some embodiments of the present invention. At 205, data identifying an MR pulse sequence is obtained using one or more techniques known in the art. In one embodiment, the MR pulse sequence comprises a multi-echo incoherent steady state pulse sequence with echo times selected by a pseudorandom number generator. In other embodiments, the process 200 may be adjusted to operate with different kinds of pulse sequences through other appropriate signal models.

At 210, measurement values comprising a range of fat fraction values and transverse relaxation rates are determined for an area of interest within a subject's anatomy. The measurement values may be selected, for example, based on literature associated with the diseases of interest (e.g., common liver diseases). The range of fat fraction values corresponds to the ratio of fat proton density to total fat and water proton density within the anatomy. In one embodiment, the range of fat fraction values range from 0% to 90% in increments of 1%. The transverse relaxation rate corresponds to the inverse of $T_2^*$ ($T_2$ Star), a characteristic time constant that describes the decay of transverse magnetization, taking into account the inhomogeneity in static magnetic fields and the spin relaxation in the human body. In one embodiment, transverse relaxation values range from 0 Hz to 600 Hz in increments of 5 Hz. The measurement values may also include items germane to the MRI system such as, without limitation, magnetic field offset values.

Continuing with reference to FIG. 2, at 215, a reference signal is generated for the MR pulse sequence via simulation based on the measurement data. In some embodiments, an incoherent set of echo times are generated to sample time signals. Then, during the simulation, the reference signal is acquired at the incoherent set of echo times. In some embodiments, the Bloch equations for magnetic resonance are used to generate the signal. In other embodiments, other techniques may be used including, for example, techniques based on in quantum mechanics which account for the motion of individual nuclear magnetic moments. Then, at 220, the generated reference signal and its corresponding reference data (e.g., fat fraction value, transverse relaxation rate, etc.) are stored in a repository (also referred to herein as a "library"). The repository may be embodied in any storage medium. For example, in one embodiment, a database of reference signal entries is maintained, with each entry including a reference signal and its corresponding reference data. Steps 210, 215, and 220 may be repeated for additional measurement values, thereby supplementing the repository for a range of measurement values. The number of times the process repeats may be dependent on the measurement values used. For example, in one embodiment, the range of fat fraction values range from 0% to 90% in increments of 1% and the transverse relaxation values range from 0 Hz to 600 Hz in increments of 5 Hz. Thus, there are 91 possible fat fraction values and 121 possible transverse relaxation rate values. Accounting for each permutation of fat fraction and transverse relaxation rate, 91*121=11011 reference signals would be generated and stored in the repository. It should be noted that the manner in which reference signals are generated for these permutations may differ in various embodiments. For example, in one embodiment, a range of transverse relaxation rate values is selected first. Then, for each transverse relaxation rate value, a range of fat fraction values is selected and iterated over to generate the reference signal. Conversely, in other embodiments, the range of fat fraction values is selected first. Then, for each fat fraction value, a range of transverse relaxation rate values is iterated over to generate the reference signal. Returning to FIG. 2, the process 200 ends at 225 when all reference signals have been generated for the range of fat fraction and transverse relaxation rate values.

In some embodiments, additional information corresponding to each reference signal may be added to the repository. For example, this information may include, without limitation, spectroscopic signals of interest, motion parameters, other relaxation parameters, RF transmit fields, RF receive fields, and information which allows for incoherent sampling of the reference signal. This information may be used, for example, to further refine the matching of a test signal with reference signal or to enhance the fat and/or iron estimation process.

In some embodiments, various techniques are used to improve the computational efficiency of the library generated in process 200. For example, in one embodiment the sampling rate of the fat fraction and/or transverse relaxation rate may be adjusted to generate and store more or less reference signals in the repository. In some embodiments, the time required to create the repository can be reduced via parallelization or other similar methods.

Figure 3:
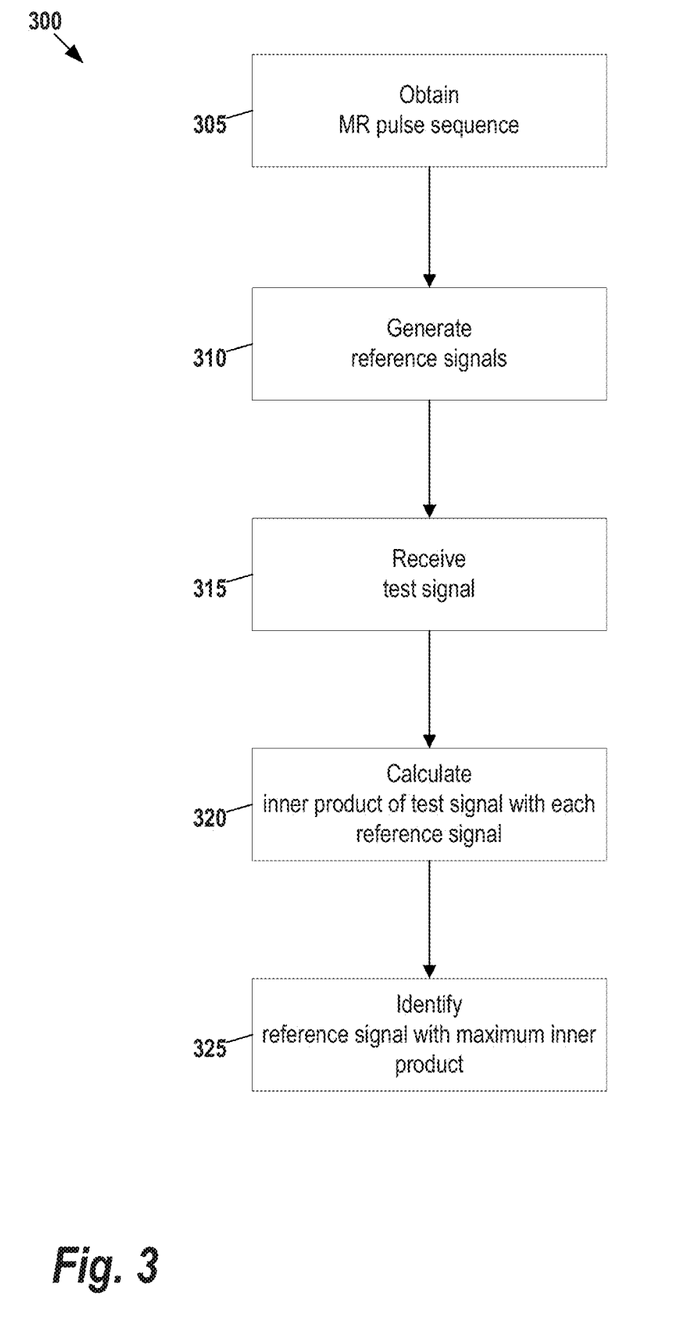
FIG. 3 provides an overview of a process for concurrently estimating fat and iron, according to some embodiments of the present invention.

FIG. 3 provides an overview of a process 300 for concurrently estimating fat and iron, according to some embodiments of the present invention. At 305, data identifying an MR pulse sequence is obtained (e.g., as described above with reference to step 205 of FIG. 2). Next, at 310, a repository of reference signals is generated based, in part, on the MR pulse sequence. An example process 200 for generating this reference signal repository is described in FIG. 2. Then, at 315, a test signal is received. This test signal may be acquired from a variety of sources including, without limitation, a patient, a volunteer, an animal model, or a physical or numerical phantom. For example, in one embodiment, the test signal is a response signal resulting from applying the MR pulse sequence to a test patient having a certain clinical condition (e.g., an obese patient). In some embodiments, the test signal is acquired in advance of the generation of the reference signal 310 and recorded in a storage medium for later use when executing the process 300 described in FIG. 3. In other embodiments, the test signal is acquired at 315 during the process 300. The acquisition of the test signal may employ multi-channel data provided by multiple receive coils or multi-element arrays, for example of system 10 of FIG. 1.

Continuing with reference to FIG. 3, at 320, the inner product of the test signal and each reference signal is calculated using any technique known in the art. As is understood in the art, the angle between two signals provides a comparison of how closely the two signals are aligned. Specifically, if the inner product of the test signal and a particular reference signal is large, the two signals are approximately the same. Thus, to determine the reference signal that is closest to the test signal, at 325 the reference signal with the largest inner product is identified. The computational efficiency of 320 and 325 can be improved by, for example, by allowing sampling of the library and accepting inner product values within a predetermined tolerance. In the event that two reference signals have identical inner products, one of the reference signals may be randomly selected or additional criteria associated with the reference signals may be used in making the selection. The fat fraction and transverse relaxation rate that correspond to the selected reference signal may then be used as the estimated fat fraction and transverse relaxation rate respectively.

A graphical user interface (GUI) may be used in the processes 200 and 300 (described in FIGS. 2 and 3, respectively) to allow a user to customize various values, as well as view the intermediary and final results of the processes. For example, in some embodiments, the range of fat fraction values and/or the increment between respective values selected at 210 in FIG. 2 may be adjusted via the GUI. Similarly, in some embodiments, the range of transverse relaxation rate values and/or the increment between respective values can be adjusted via the GUI. Additionally, in some embodiments, the process 300 provides an indication of how closely the test signal matched the repository. This information may be provided, for example, in the GUI in connection with each individual reference signal or a single value may be provided indicating how closely the test signal matched the repository overall. These values may be used, for example, to estimate the accuracy of the selected fat fraction and transverse relaxation rate.

Figure 4:
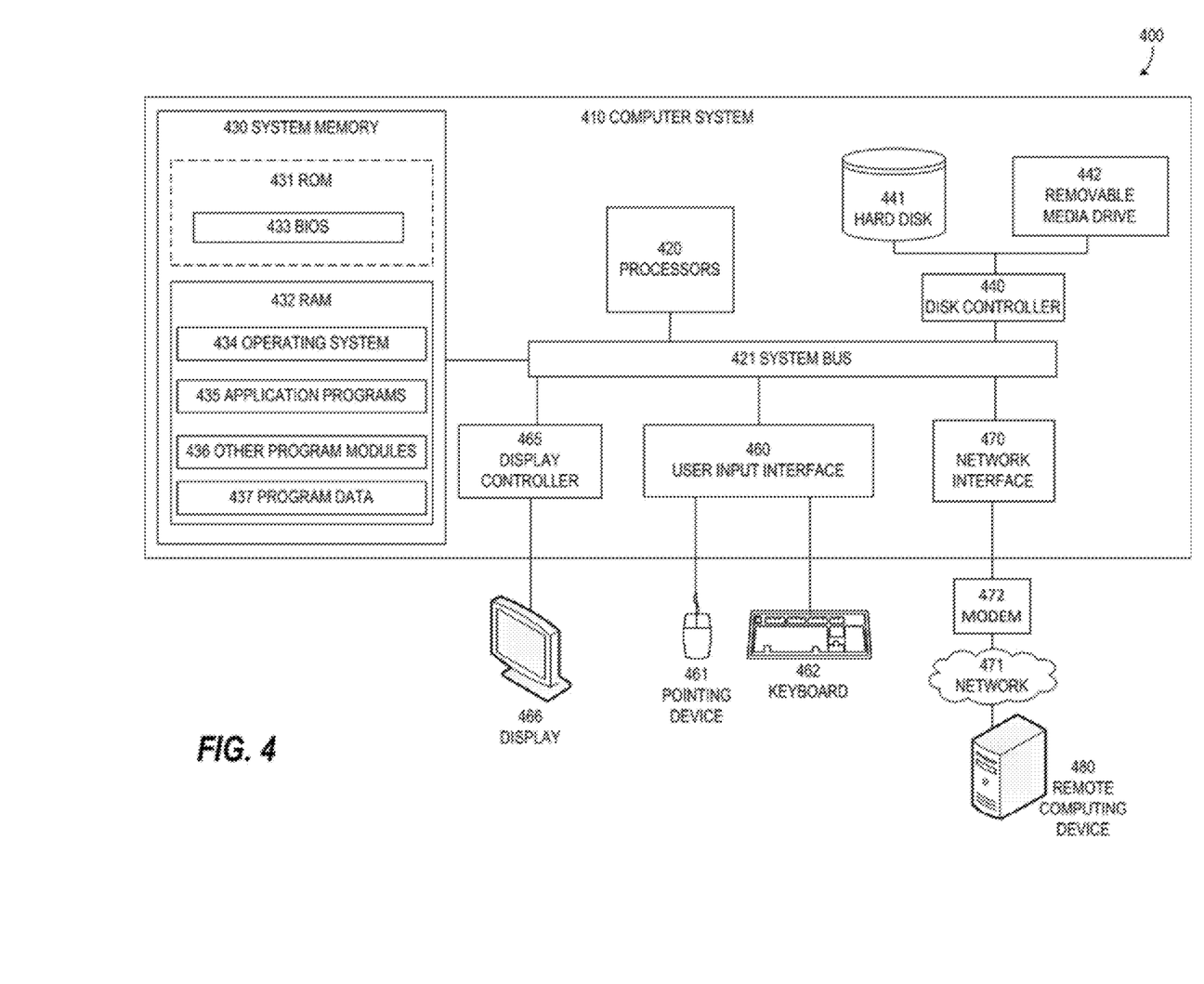
FIG. 4 illustrates an exemplary computing environment within which embodiments of the invention may be implemented.

FIG. 4 illustrates an exemplary computing environment 400 within which embodiments of the invention may be implemented. Computing environment 10 may include computer system 410, which is one example of a computing system upon which embodiments of the invention may be implemented. Computers and computing environments, such as computer 410 and computing environment 400, are known to those of skill in the art and thus are described briefly here.

As shown in FIG. 4, the computer system 410 may include a communication mechanism such as a bus 421 or other communication mechanism for communicating information within the computer system 410. The system 410 further includes one or more processors 420 coupled with the bus 421 for processing the information.

The processors 420 may include one or more central processing units (CPUs), graphical processing units (GPUs), or any other processor known in the art. More generally, a processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and be conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

Continuing with reference to FIG. 4, the computer system 410 also includes a system memory 430 coupled to the bus 421 for storing information and instructions to be executed by processors 420. The system memory 430 may include computer readable storage media in the form of volatile and/or nonvolatile memory, such as read only memory (ROM) 431 and/or random access memory (RAM) 432. The system memory RAM 432 may include other dynamic storage device(s) (e.g., dynamic RAM, static RAM, and synchronous DRAM). The system memory ROM 431 may include other static storage device(s) (e.g., programmable ROM, erasable PROM, and electrically erasable PROM). In addition, the system memory 430 may be used for storing temporary variables or other intermediate information during the execution of instructions by the processors 420. A basic input/output system 433 (BIOS) containing the basic routines that help to transfer information between elements within computer system 410, such as during start-up, may be stored in ROM 431. RAM 432 may contain data and/or program modules that are immediately accessible to and/or presently being operated on by the processors 420. System memory 430 may additionally include, for example, operating system 434, application programs 435, other program modules 436 and program data 437.

The computer system 410 also includes a disk controller 440 coupled to the bus 421 to control one or more storage devices for storing information and instructions, such as a magnetic hard disk 441 and a removable media drive 442 (e.g., floppy disk drive, compact disc drive, tape drive, and/or solid state drive). The storage devices may be added to the computer system 410 using an appropriate device interface (e.g., a small computer system interface (SCSI), integrated device electronics (IDE), Universal Serial Bus (USB), or FireWire).

The computer system 410 may also include a display controller 465 coupled to the bus 421 to control a display or monitor 465, such as a cathode ray tube (CRT) or liquid crystal display (LCD), for displaying information to a computer user. The computer system includes an input interface 460 and one or more input devices, such as a keyboard 461 and a pointing device 462, for interacting with a computer user and providing information to the processor 420. The pointing device 462, for example, may be a mouse, a light pen, a trackball, or a pointing stick for communicating direction information and command selections to the processor 420 and for controlling cursor movement on the display 466. The display 466 may provide a touch screen interface which allows input to supplement or replace the communication of direction information and command selections by the pointing device 461.

The computer system 410 may perform a portion or all of the processing steps of embodiments of the invention in response to the processors 420 executing one or more sequences of one or more instructions contained in a memory, such as the system memory 430. Such instructions may be read into the system memory 430 from another computer readable medium, such as a hard disk 441 or a removable media drive 442. The hard disk 441 may contain one or more datastores and data files used by embodiments of the present invention. Datastore contents and data files may be encrypted to improve security. The processors 420 may also be employed in a multi-processing arrangement to execute the one or more sequences of instructions contained in system memory 430. In alternative embodiments, hard-wired circuitry may be used in place of or in combination with software instructions. Thus, embodiments are not limited to any specific combination of hardware circuitry and software.

As stated above, the computer system 410 may include at least one computer readable medium or memory for holding instructions programmed according embodiments of the invention and for containing data structures, tables, records, or other data described herein. The term "computer readable medium" as used herein refers to any medium that participates in providing instructions to the processor 420 for execution. A computer readable medium may take many forms including, but not limited to, non-transitory, non-volatile media, volatile media, and transmission media. Non-limiting examples of non-volatile media include optical disks, solid state drives, magnetic disks, and magneto-optical disks, such as hard disk 441 or removable media drive 442. Non-limiting examples of volatile media include dynamic memory, such as system memory 430. Non-limiting examples of transmission media include coaxial cables, copper wire, and fiber optics, including the wires that make up the bus 421. Transmission media may also take the form of acoustic or light waves, such as those generated during radio wave and infrared data communications.

The computing environment 400 may further include the computer system 420 operating in a networked environment using logical connections to one or more remote computers, such as remote computer 480. Remote computer 480 may be a personal computer (laptop or desktop), a mobile device, a server, a router, a network PC, a peer device or other common network node, and typically includes many or all of the elements described above relative to computer 410. When used in a networking environment, computer 410 may include modem 472 for establishing communications over a network 471, such as the Internet. Modem 472 may be connected to system bus 421 via user network interface 470, or via another appropriate mechanism.

Network 471 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 410 and other computers (e.g., remote computing system 480). The network 471 may be wired, wireless or a combination thereof. Wired connections may be implemented using Ethernet, Universal Serial Bus (USB), RJ-6, or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 471.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the UI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

I claim:

1. A computer-implemented method for concurrently estimating an amount of fat and iron in anatomical tissue from magnetic resonance (MR) signal data, the method comprising:
   receiving a test signal representative of the anatomical tissue acquired using a MR pulse sequence type;
   generating a repository of reference signal data comprising a plurality of reference signals derived by an MR signal simulation for a plurality of different transverse relaxation rates, a plurality of different fat fractions, and the MR pulse sequence type;
   identifying a first reference signal in the plurality of reference signals, the first reference signal providing a best match to the test signal based on one or more matching criteria;
   searching the repository to determine a first transverse relaxation rate and a first fat fraction associated with the first reference signal; and
   estimating the amount of fat and iron in the anatomical tissue based on the first transverse relaxation rate and the first fat fraction.

2. The method of claim 1, wherein the MR signal simulation includes application of a Bloch function for magnetic resonance.

3. The method of claim 1, wherein the one or more matching criteria comprise a measure of signal similarity determined by a mathematical product calculation.

4. The method of claim 3, wherein identifying the first reference signal in the plurality of reference signals, the first reference signal providing the best match to the test signal based on one or more matching criteria, comprises:
   for each of the plurality of reference signals, calculating a mathematical product value of the test signal with the respective reference signal; and
   determining that the first reference signal has a maximum mathematical product value among the plurality of reference signals.

5. The method of claim 1, further comprising:
   generating a plurality of magnetic field offset values corresponding to the different transverse relaxation rates; and
   storing the plurality of magnetic field offset values in the repository of reference signal data.

6. The method of claim 1, further comprising:
   generating an incoherent set of echo times for use in acquiring the reference signals; and
   deriving the reference signals by the MR signal simulation at the incoherent set of echo times.

7. The method of claim 6, wherein receiving the test signal representative of the anatomical tissue acquired using the pulse sequence type comprises:
   acquiring the test signal at the set of echo times.

8. A system for concurrently estimating an amount of fat and iron in anatomical tissue from magnetic resonance (MR) signal data, the system comprising:
   an input processor configured to receive a test signal representative of the anatomical tissue acquired using a MR pulse sequence type;
   a repository of reference signal data comprising a plurality of reference signals derived by MR signal simulation for a plurality of different transverse relaxation rates, a plurality of different fat fractions, and the MR pulse sequence type;
   an image data processor configured to:
      identify a first reference signal in the plurality of reference signals providing a best match to the test signal based on one or more matching criteria,
      search the repository to determine a first transverse relaxation rate and a first fat fraction associated with the first reference signal, and
      estimate the amount of fat and iron in the anatomical tissue based on the first transverse relaxation rate and the first fat fraction.

9. The system of claim 8, the image data processor identifies the first reference signal in the plurality of reference signals providing the best match to the test signal based on one or more matching criteria by a matching process comprising:
   for each of the plurality of reference signals, calculating a mathematical product value of the test signal with the respective reference signal; and
   determining that the first reference signal has a maximum mathematical product value among the plurality of reference signals.

10. The system of claim 8, further comprising:
    a simulation processor configured to generate the plurality of reference signals.

11. The system of claim 10, wherein the simulation processor generates the plurality of reference signals using a Bloch function.

12. A system according to claim 10, wherein the simulation processor is further configured to generate a range of fat fraction values for corresponding different transverse relaxation rates.

13. A system according to claim 12, wherein the simulation processor is further configured to generate a plurality of magnetic field offset values for corresponding different transverse relaxation rates.

14. The system of claim 10, wherein the simulation processor is further configured to:
    generate an incoherent set of echo times for use in acquiring the reference signals; and
    generate the repository of reference signal data at the incoherent set of echo times using a signal model.

15. A computer-implemented method for concurrently estimating fat and iron in anatomical tissue using magnetic resonance (MR) signal data, the method comprising:
    receiving, by an image processing computer, MR signal data representative of a portion of patient anatomy;
    generating, by the image processing computer, a library of reference signal entries, each reference signal entry comprising a reference signal, an associated transverse relaxation value, and an associated fat fraction value;
    receiving, by the image processing computer, a test signal;
    for each reference signal entry in the library of reference signal entries, calculating an inner product value of the test signal and the respective reference signal entry's corresponding reference signal;
    identifying, by the image processing computer, a first reference signal entry associated with a maximum inner product value; and
    estimating, by the image processing computer, a test transverse relaxation rate value and a test fat fraction value based on a first associated transverse relaxation value and a first associated fat fraction value corresponding to the first reference signal entry.

16. The method of claim 15, wherein generating the library of reference signals comprises:
  receiving, by the image processing computer, an MR pulse sequence;
  selecting, by the image processing computer, a range of transverse relaxation rate values; and
  for each transverse relaxation value in the range of transverse relaxation rate values, performing an iterative process comprising:
    selecting, by the image processing computer, a plurality of fat fraction values,
    performing a MR simulation to generate a reference signal for the respective transverse relaxation value and each fat fraction value, and
    creating a plurality of entries in the library of reference signals, each entry comprising the generated reference signal, the respective transverse relaxation value, and one of the plurality of fat fraction values.

17. The method of claim 16, wherein the range of transverse relaxation rate values comprises a plurality of transverse relaxation rate values ranging from 0 Hz to 600 Hz in increments of 5 Hz.

18. The method of claim 15, wherein generating the library of reference signals comprises:
  receiving, by the image processing computer, an MR pulse sequence;
  selecting, by the image processing computer, a range of fat fraction values; and
  for each fat fraction value in the range of fat fraction values, performing an iterative process comprising:
    selecting, by the image processing computer, a plurality of transverse relaxation values,
    performing a MR simulation to generate a reference signal for each transverse relaxation value and the respective fat fraction value, and
    creating plurality of entries in the library of reference signals, each entry comprising the generated reference signal, one of the transverse relaxation values, and the respective fat fraction value.

19. The method of claim 18, wherein the range of fat fraction values comprises a plurality of fat fraction values ranging from 0% to 90% in increments of 1%.

20. The method of claim 15, wherein each reference signal entry in the library of reference signal entries further comprises one or more magnetic field offset values.

* * * * *